(12) United States Patent
Bonecker

(10) Patent No.: US 9,804,095 B2
(45) Date of Patent: Oct. 31, 2017

(54) TEST SET FOR A PHOTOMETRIC MEASURING DEVICE, AND PHOTOMETRIC MEASURING METHOD FOR A SAMPLE LIQUID

(71) Applicant: Gerhard Bonecker, Baar (CH)

(72) Inventor: Gerhard Bonecker, Baar (CH)

( * ) Notice: Subject to any disclaimer, the term of this patent is extended or adjusted under 35 U.S.C. 154(b) by 222 days.

(21) Appl. No.: 14/440,737

(22) PCT Filed: Oct. 22, 2013

(86) PCT No.: PCT/EP2013/072037
§ 371 (c)(1),
(2) Date: May 5, 2015

(87) PCT Pub. No.: WO2014/072170
PCT Pub. Date: May 15, 2014

(65) Prior Publication Data
US 2015/0285741 A1  Oct. 8, 2015

(30) Foreign Application Priority Data
Nov. 6, 2012 (AT) .............................. A 50489/2012

(51) Int. Cl.
*B01F 15/00* (2006.01)
*G01N 21/75* (2006.01)
(Continued)

(52) U.S. Cl.
CPC ......... *G01N 21/75* (2013.01); *B01F 15/0205* (2013.01); *B01F 15/0215* (2013.01);
(Continued)

(58) Field of Classification Search
CPC ......... B01L 2200/0605; B01L 2200/10; B01L 2300/041; B01L 2300/044;
(Continued)

(56) References Cited

U.S. PATENT DOCUMENTS 7,540,056 B2   6/2009   Dotterman et al.
8,443,848 B2   5/2013   Hentzel et al.
(Continued)

FOREIGN PATENT DOCUMENTS

DE   2441724   4/1975

*Primary Examiner* — Jennifer Wecker
(74) *Attorney, Agent, or Firm* — Dykema Gossett PLLC

(57) ABSTRACT

The invention relates to a test set (1) for a photometric measuring device, comprising a mixing container (2) which has a filling opening (3) and comprising a metering container (8) which can be sealingly inserted into the filling opening (3) of the mixing container (2) and which contains a liquid reagent (13) in a closed cavity (9). The cavity (9) has a closure plunger (11), which can be moved axially in the cavity (9), at a first end of the metering container (8), said closure plunger generating a specifiable filling pressure in the reagent (13), and the metering container (8) has a closure membrane (10) at a second metering container and which can be inserted into the mixing container (2). According to the invention, the closure membrane (10) is equipped with a predetermined breaking point (20) which breaks open when the filling pressure is exceeded in a defined manner as a result of an axial movement of the closure plunger (11), said predetermined breaking point (20) of the closure membrane (10) being formed as a linearly extending material taper of the closure membrane (10), wherein the taper is arranged eccentrically in the region of an opening (24) in the base (23) of the substantially cylindrical metering container (8).

14 Claims, 3 Drawing Sheets

(51) Int. Cl.
*G01N 21/03* (2006.01)
*B01L 3/00* (2006.01)
*B01F 15/02* (2006.01)
*G01N 35/02* (2006.01)
*G01N 1/02* (2006.01)
*B01F 13/08* (2006.01)

(52) U.S. Cl.
CPC .......... *B01F 15/0224* (2013.01); *B01L 3/502* (2013.01); *B01L 3/508* (2013.01); *B01L 3/523* (2013.01); *G01N 21/03* (2013.01); *B01F 13/0818* (2013.01); B01L 3/5029 (2013.01); B01L 3/5082 (2013.01); B01L 3/50825 (2013.01); B01L 2200/025 (2013.01); B01L 2200/028 (2013.01); B01L 2200/0605 (2013.01); B01L 2200/10 (2013.01); B01L 2300/041 (2013.01); B01L 2300/044 (2013.01); B01L 2300/047 (2013.01); B01L 2300/049 (2013.01); B01L 2300/0672 (2013.01); B01L 2300/0832 (2013.01); B01L 2300/12 (2013.01); B01L 2400/0406 (2013.01); B01L 2400/0478 (2013.01); B01L 2400/0487 (2013.01); B01L 2400/0638 (2013.01); B01L 2400/0683 (2013.01); G01N 2001/028 (2013.01)

(58) Field of Classification Search
CPC .......... B01L 2300/047; B01L 2300/12; B01L 2400/0406; B01L 2400/0478; B01L 2400/0487; B01L 2400/0683; B01L 3/502; B01L 3/508; B01L 3/50825; B01L 3/523; B01L 2300/022; B01L 2300/042; B01L 2200/142; B01L 2300/049; B01L 2400/0638; B01L 2200/025; B01L 2200/028; B01L 2300/0672; G01N 21/75; G01N 21/03; G01N 2001/028; B01F 13/0022; B01F 13/0818; B01F 15/0205; B01F 15/0224

See application file for complete search history.

(56) References Cited

U.S. PATENT DOCUMENTS

| | | | |
|---|---|---|---|
| 8,906,310 B2 | 12/2014 | Bonecker | |
| 2006/0088446 A1 | 4/2006 | Heck et al. | |
| 2008/0260581 A1* | 10/2008 | Rosman | B01L 3/5029 422/68.1 |
| 2009/0026474 A1* | 1/2009 | Blumel | H01L 33/58 257/98 |
| 2009/0155923 A1 | 6/2009 | Bonecker | |
| 2010/0180773 A1* | 7/2010 | Hentzel | A47J 42/40 99/275 |
| 2010/0189602 A1* | 7/2010 | Baeuerle | B01D 15/206 422/70 |
| 2010/0261223 A1* | 10/2010 | Margraf | B01L 3/502753 435/29 |
| 2011/0104737 A1* | 5/2011 | Bonecker | B01F 13/002 435/29 |
| 2012/0214251 A1* | 8/2012 | Bonecker | B01F 13/0244 436/164 |

* cited by examiner

TEST SET FOR A PHOTOMETRIC MEASURING DEVICE, AND PHOTOMETRIC MEASURING METHOD FOR A SAMPLE LIQUID

BACKGROUND OF THE INVENTION

The invention relates to a test set for a photometric measuring device, including a mixing container which has a filling opening, and a dosing container which can be inserted in a sealing manner into the filling opening of the mixing container and which contains a liquid reagent in a closed cavity, wherein the cavity includes a closing plunger at a first end of the dosing container which can be moved axially in the cavity, the closing plunger generating a predeterminable filling pressure in the reagent, and the dosing container includes a closure membrane at a second end of the dosing container which can be inserted into the mixing container. The invention further relates to a photometric measuring method for a sample liquid.

THE PRIOR ART

In many medical tests the sample to be measured needs to be brought into contact at first with a first liquid in order to condition the sample, prepare the same for the measurement, or initiate a first chemical or biological reaction. In a second step a second liquid is added in order to transfer the analyte of the sample to be determined to a state suitable for photometric measurement, or to initiate a second chemical or biological reaction. For example, in a so-called CRP measurement (C-reactive protein) which is used for distinguishing viral or bacterial inflammations, a blood sample is mixed with a lysis reagent and thereafter a latex reagent is added and mixed, with the chemical reaction being measured with the help of a photometer.

A test set of the kind mentioned above is known for example from WO 2007/053870 A2. The test set comprises a mixing container and a dosing container that can be inserted into the mixing container. The mixing container is equipped with a closing element which can be removed from a filling opening and contains a first liquid, with the dosing container being insertable into the filling opening of the mixing container after the removal of the closing element and the addition of the sample liquid to the first liquid. The dosing container contains a second liquid in a sealed cavity, with the cavity being sealed on the one side by a sealing plunger on the one side and by a movable plug on the other side, which after pressurizing the sealing plunger conveys the second liquid together with the movable plug into the interior of the mixing container. After the mixture of the sample with the first liquid and the second liquid, the mixing container is used in a photometric analyzer, whereupon the sample ingredients are photometrically measured. The known methods are susceptible to errors because precise sample quantities need to be supplied which are precisely required for the respective test set and the respective medical test.

Furthermore, the dosing container according to AT 502 693 A1 can also be sealed by a valve or a membrane (not shown in greater detail) instead of the plug, wherein the membrane is destroyed after pressurizing the second liquid in the interior of the dosing container and the liquid exits to the interior of the mixing container. It has been recognized, however, that an uncontrolled, non-reproducible destruction or tearing of the membrane by pressurization leads to non-reproducible measurement results of the test set because the liquid exits in an uncontrolled manner from the dosing element and droplets of the liquid adhere to the walls and the edges of the membrane.

A sample-taking and measuring element is known from WO 2005/071388 A1 which consists of several cylindrical compartments which are inserted into each other in an axially displaceable way, with their inside spaces being sealed in the initial position by a penetrable membrane. Two of the elements contain reactants and a sample can be introduced in the third element by a swab. The compartments are slid into each other by exerting pressure on the two outer elements, as a result of which the membranes tear at the connecting points and simultaneously the two reagent liquids are mixed with the sample. Analysis occurs either by optical inspection or by using a measuring device.

DE 24 41 724 A1 describes an analytic cartridge for photospectrometric measurements, comprising a first container for receiving a first liquid, with the container being sealed at first by a closing element. After the removal of the closing element, the sample to be analyzed is placed in the container and a container insert is then placed on the same which comprises a reagent liquid in an auxiliary chamber. The auxiliary chamber is provided with a cylindrical tappet which in the initial position protrudes beyond the container insert and which, when pressed down, tears open a membrane of the auxiliary chamber with the help of a cutting edge on the front side and thus releases the second liquid from the auxiliary chamber into the container with the first liquid. Once the liquids have dissolved and are mixed completely, the container is heated in the manner required for the analytic method and the sample is measured in a photometric way.

It is the object of the invention to provide a photometric measuring method for a sample liquid which is extremely simple to handle, wherein an improved test set shall be used which can be produced in a simpler and more cost-effective manner. Furthermore, precise dosing of the individual reagent and the sample liquid shall be possible in a simple way.

SUMMARY OF THE INVENTION

This object is achieved in accordance with the invention such a way that the closure membrane is provided with a predetermined breaking point, which breaks open when the filling pressure is exceeded in a defined manner as a result of an axial movement of the dosing plunger, said predetermined breaking point of the closure membrane being formed as a linearly extending material taper of the closure membrane, which taper is arranged eccentrically in the region of an opening in the base of the substantially cylindrical dosing container. The test set in accordance with the invention also leads to reproducible measurement results even in the case of small sample quantities because the closure membrane breaks open on the linearly extending material taper in a defined and reproducible manner and allows the reagent to exit to the mixing container in an optimal geometry of the liquid jet.

The closure membrane can preferably be injected by means of 2K injection molding technology directly onto the end of the dosing container that is insertable into the mixing container. For example, the filling pressure in the cavity of the dosing container can lie in a range of <2 bars after filling by a machine and the first pressure of the predetermined breaking point of the closure membrane can be predetermined in the range of >3 bars, so that during a further axial displacement of the closing plunger in the direction of the closure membrane the burst pressure is exceeded and the reagent exits to the mixing container.

According to an embodiment in accordance with the invention, the closure membrane can comprise a tapering, funnel-shaped, integrally attached formed portion which carries away from the dosing container and which guides the reagent exiting from the dosing container toward the base area of the mixing container.

Further advantages in production are obtained when the dosing container comprises, in its sealing area toward the filling opening of the mixing container, a sealing collar which is injected by means of 2K injection molding technology, wherein the closure membrane and the sealing collar are connected to each other by a web extending along the dosing container and can be injected thereon in one working step.

By using an integrated sample-taking system (also see WO 2011/047902 A1) with a capillary (end-to-end capillary) which is open on both sides, the test set will become substantially more user-friendly for the user according to one embodiment. The capillary will automatically fill after sample contact with the volume of between 5 µl and 25 µl for example, which is predetermined by the inner diameter and the length of the capillary, so that the user does not have to perform any separate pipetting steps. The user merely needs to touch the surface of the sample liquid with the end of the capillary tube, with the tube filling up by the capillary effect and with precisely the sample volume predetermined for the respective sample measurement being sucked in.

A measuring method in accordance with the invention, in which a sample liquid is mixed with a reagent present in a mixing container and a liquid reagent, wherein the liquid reagent is present in a dosing container whose cavity at one end is sealed by an axially displaceable closing plunger and at the other end by a closure membrane, is characterized by the following steps:
  opening of the mixing container;
  adding the sample liquid to the mixing container;
  inserting the dosing container into a filling opening of the mixing container;
  mixing of the sample liquid with the reagent to form a preliminary product;
  introducing a liquid reagent from the dosing container into the mixing container, with pressure being exerted on the reagent by the axially displaceable closing plunger until the closure membrane arranged on the dosing container breaks open at a predetermined breaking point and discharges a jet of the reagent exiting under pressure into the mixing container;
  mixing of the preliminary product and the liquid reagent to an end product;
  photometric measurement of the chemical reaction in an analyzer, and
  calculating the concentration of at least one sample ingredient of the end product.

The reagent can be present in the mixing container in a liquid, gel-like, freeze-dried, powder or tablet form, or as a wall film.

A photometric calibration measurement can be carried out after the mixing of the reagent with the sample liquid.

BRIEF DESCRIPTION OF THE DRAWINGS

The invention will be explained below in greater detail by reference to the drawings, wherein.

DETAILED DESCRIPTION OF THE DEPICTED EMBODIMENT

Figure 1:
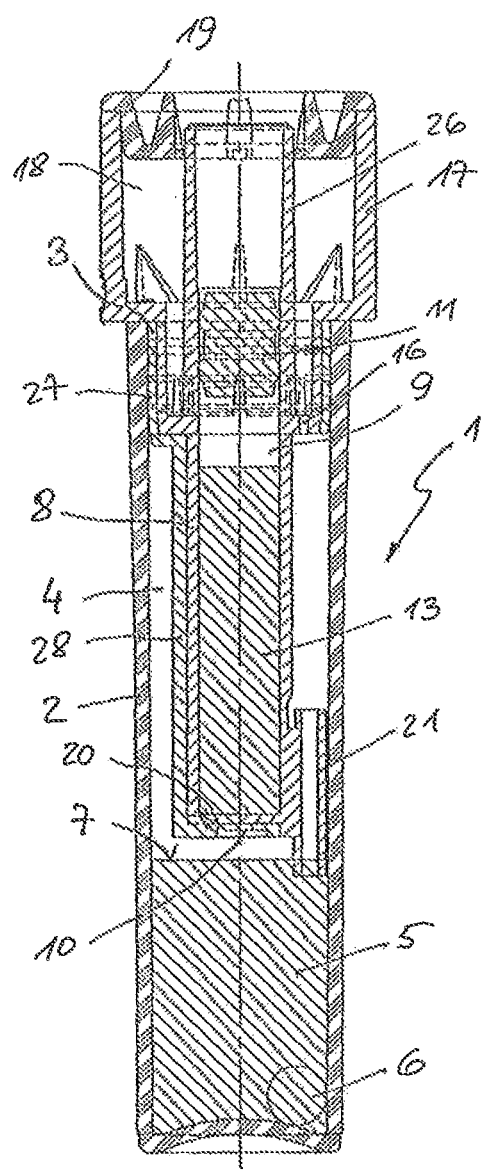
FIG. 1 shows a sectional view of a test set in accordance with the invention with a mixing container and a dosing container inserted into the mixing container.

The embodiment of the test set 1 shown in FIGS. 1 to 4 is provided for use in a photometric measuring device or analyzer, as described in detail in WO 2007/053380 A2 for example.

The filling opening 3 of the tubular mixing container 2 of the test set 1 is sealed in a sterile manner at first by means of a removable closing element (not shown), wherein, according to the illustrated embodiment, a first liquid 5 is disposed in the interior 4 as well as a magnetic stirrer or a steel ball 6. An air space is disposed above the first liquid 5, with the surface of the liquid being indicated with reference numeral 7.

The dosing container 8, which can be inserted into the mixing container 2, comprises a cylindrical cavity 9 which is sealed at one end (on the outlet side) by a closure membrane 10. An axially displaceable closing plunger 11 is disposed on the opposite side in the cavity 9, which closing plunger can be displaced axially into the cavity and on which an actuating stamp of an analyzer (not shown) can exert pressure. When the closing plunger 11 is inserted, a predeterminable filling pressure is generated in the reagent 13 during filling of the dosing container with a reagent. The closure membrane 10 is provided with a predetermined breaking point 20 which, upon exceeding a defined filling pressure, breaks open, triggered by an axial displacement of the closing plunger 11.

The predetermined breaking point 20 of the closure membrane 10 can be arranged for example as a linear extending material taper of the outer membrane 10 (see FIGS. 3 and 4), wherein the closure membrane 10 is preferably injected by means of 2K injection molding technology onto the end of the dosing container 8 which can be inserted in the mixing container 2. The dosing container 8 consists of polypropylene (PP), and the co-extruded closure membrane 10 consists of a cross-linked thermoplastic elastomer on the basis of olefin (TPE-V) for example.

The material taper is preferably arranged eccentrically in the region of an elongated opening 24 in the base 23 of the substantially cylindrical dosing container 8 in order to ensure optimal discharge of the reagent from the dosing container.

The axially displaceable closing plunger 11 is entirely arranged within the dosing container 8 and is actuated by a stamp of the analyzer. Erroneous actuation by the laboratory staff is thus substantially excluded. The cavity 9 has a slightly smaller inside diameter in the region of the seal seat of the closing plunger 11 than in a collar region 26 situated outside of the seal seat. During production, the closing plunger 11 can be moved without substantial friction up to the seal seat and can then be pressed into the seal seat, wherein a predeterminable filling pressure is produced in the reagent. Different filling quantities of the reagent can be realized in a simple manner by different height positions of the seal seat.

In order to keep the jet of the reagent exiting under pressure away from the walls of the mixing container 2, the closure membrane 10 can comprise according to one embodiment a tapering, funnel-shaped integral formed portion 25 (see FIGS. 5 and 6) which carries away from the dosing container 8.

Figure 2:
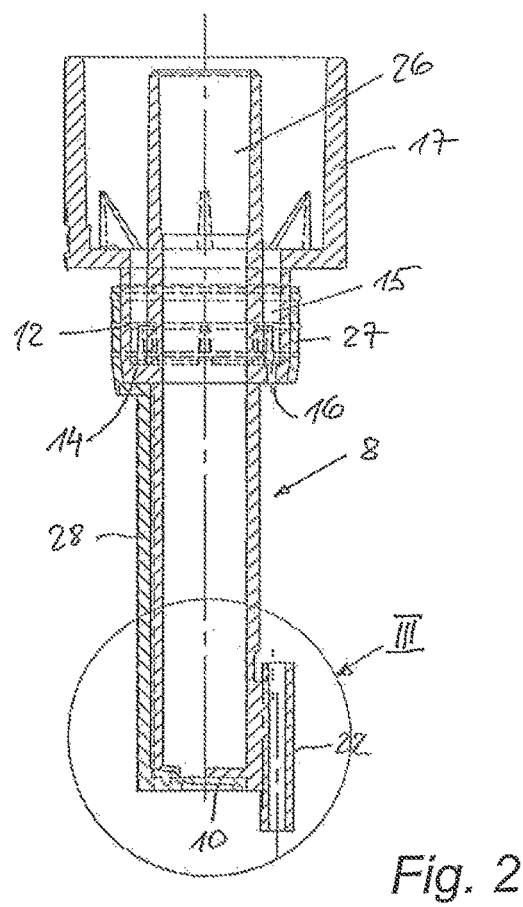
FIG. 2 shows the dosing container of the test set in accordance with the invention in a sectional view.
Figure 4:
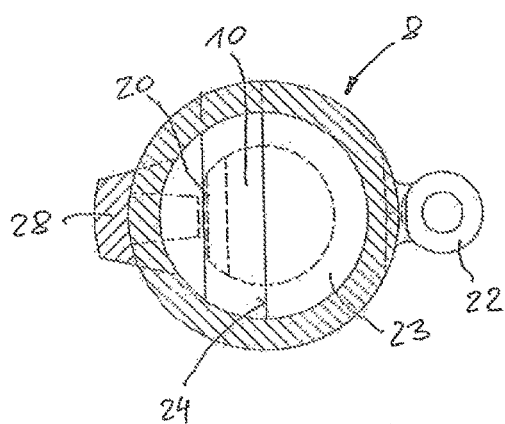
FIG. 4 shows a sectional view of the dosing container along the line IV-IV in FIG. 3.
Figure 3:
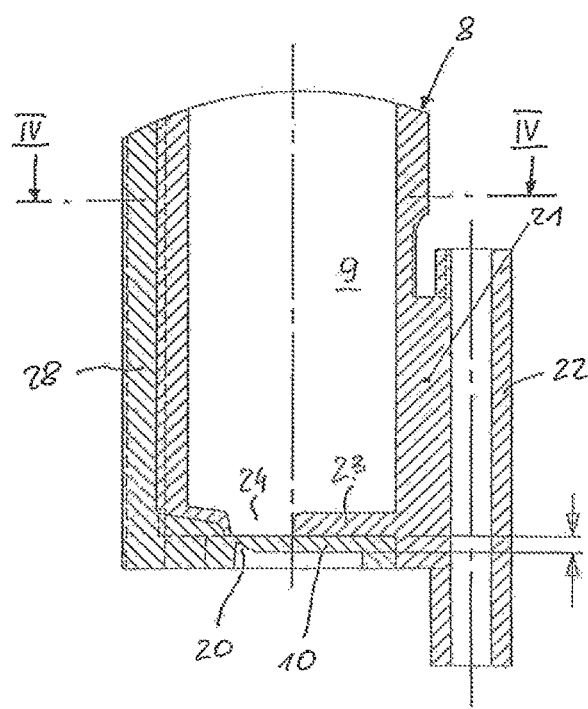
FIG. 3 shows a detail of the dosing container according to the section III in FIG. 2.
Figure 5:
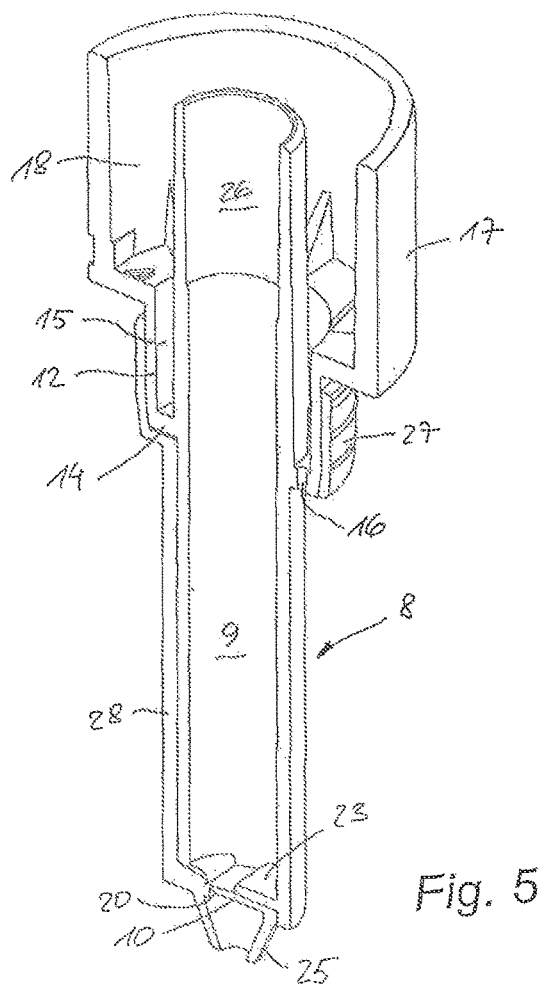
FIG. 5 shows a truncated three-dimensional illustration of the embodiment of the dosing container according to FIG. 2.
Figure 6:
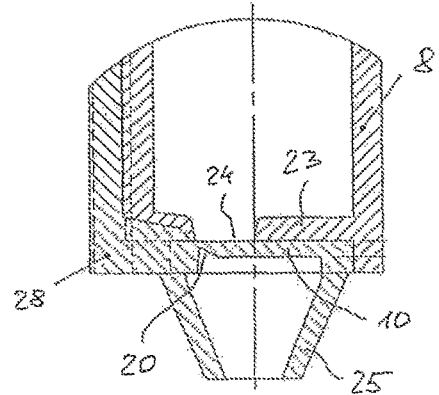
FIG. 6 shows a detail of the embodiment according to FIG. 5.

The dosing container 8 comprises a cylindrical sealing surface 12 for insertion into the mixing container 2, which sealing surface is integrally formed with an annular flange 14 on the dosing container 8 and forms an annular space 15, wherein at least one venting opening 16 is arranged in the annular flange 14 (also see FIGS. 2 and 5). When the dosing container 8 is inserted into the mixing container 2, the air displaced from the interior 4 of the dosing container 8 can escape via the gas-permeable venting open 16 which is approximately droplet-tight. For the purpose of better sealing, the dosing container 8 comprises in its sealing area towards the filling opening 3 of the mixing container 2 a sealing collar 27 which is preferably injected by means of 2K injection molding technology.

The sealing collar 27 and the closure membrane 10 preferably consist of the same synthetic material, which is set more softly in comparison with the dosing container 8, and are connected via a web 28 to each other which extends along the dosing container 8, thus simplifying production by means of 2K injection molding technology.

The dosing container 8 may comprise a sample-taking device 21 in form of a capillary 22 which is open on both sides and whose volume is precisely adjusted to the requirements of the respective measuring method and preferably lies between 5 μL and 50 μL. The user merely needs to bring the capillary 22 into contact with the surface of the sample liquid to be measured, which capillary is fixed laterally to the dosing container 8 and protrudes beyond the end region of the dosing container 8, whereupon the sample liquid is automatically sucked into the sample-taking device 21 by means of the capillary effect and in the quantity predetermined by the volume of the capillary.

A cylindrical or ergonomically optimized handle element 17 is integrally formed adjacent to the cylindrical sealing area 12 of the dosing container 8, which handle element delimits an annular space 18 and can be sealed to the outside by an annular splash protection element 19. The outlet of fluid from the test set 1 can effectively be prevented by the splash protection element 19.

Figure 7:
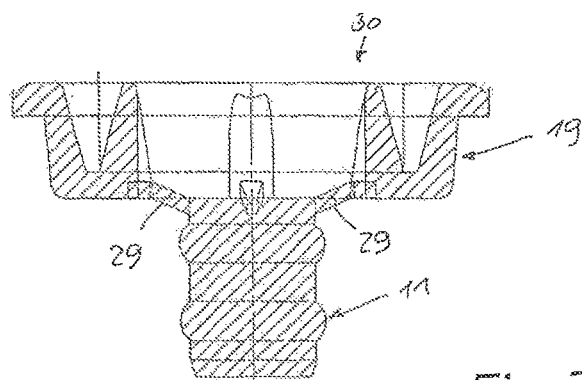
FIG. 7 shows a splash protection element for the dosing container in a sectional view.

As is shown in FIG. 7, the annular splash protection element 19 and the axially displaceable closing plunger 11 can be produced as an integral injection-molded part 30, wherein thin, breakable and severable connecting webs 29 are provided between the splash protection element 19 and the closing plunger 11. After mechanical filling of the dosing container 8 with the reagent 13, the splash protection element 29 can be inserted into the handle element 17 and the closing plunger 11 into the dosing container. The connecting webs 29 are severed during the axial displacement of the closing plunger 11 to its position in the seal seat.

First Example: INR/PT Test

INR determination is a test for the purpose of determining how fast the blood of the human will coagulate. The normal value of INR is 1; at an INR value of 4 for example blood will coagulate four times slower. A high INR value therefore means that blood coagulation does not work as well as in a healthy person.

Whole blood taken directly from the patient is used for examination and is introduced into the capillary, or blood plasma from sample tubes which are laced with citrate.

The first INR test reagent is disposed in the mixing container 2 and the second INR reagent is disposed in the dosing container 8 (liquid reagent 13, see FIG. 1).

Test Procedure of the INR Test:
  A blood sample is brought into contact with the capillary 22 of the dosing container 8 and a defined sample volume is sucked in;
  Mixing container 2 is sealed at first with a closing element and filled with lysis reagent (80 μl-150 μl);
  The closing element is removed and the dosing container (containing latex reagent) is inserted together with the integrated capillary 22 into the mixing container 2 in a sealing manner;
  The mixing container 2 and the dosing container 8 are shaken in the closed state until sample liquid exits from the end-to-end capillary 22 into the mixing container 2;
  The mixing container 2 and the dosing container 8 are inserted into a measuring device (e.g. analyzer from WO 2007/053380 A2);
  Test identification by the measuring device (by RFID chip in the packaging or on the mixing container);
  Lysis reagent and sample liquid are mixed by means of a magnetic stirrer of the measuring device (optional);
  The calibration value is measured (optional);
  Latex reagent (50 μl-200 μl) is dosed and added with the help of a stamp of the measuring device by pressure on the closing plunger 11, wherein the closure membrane 10 is broken open at its predetermined breaking point 20;
  Lysis reagent, sample fluid and latex reagent are mixed with the help of the magnetic stirrer;
  The chemical reaction is measured with the help of the photometer;
  The coagulation time is determined.
  The measuring range of the photometric measuring device is INR 0.5-INR 5 for example.

Second Example: HCY Test

From a chemical standpoint, homocysteine (HCY) belongs to the group of the so-called amino acids. In the body, homocysteine is formed from methionine, another amino acid, which is supplied with food. Homocysteine is normally degraded very rapidly, with vitamin B6 (pyridoxine), vitamin B12 (cobalamin) and folic acid being required.

Homocysteine was identified as a separate risk factor for atherosclerotic or thromboembolic events (peripheral arterial occlusive vascular disease, stroke, coronary heart disease (angina, cardiac infarction), occlusive changes to the carotid artery). In a number of further diseases such as old-age dementia, development of defects in the neural canal (spina bifida) of the child in the womb and anemia, a connection with increased homocysteine levels was established.

The first HCY reagent is located in the mixing container 2. The second HCY reagent is located in the dosing container 8. The test sequence occurs as in example 1.

Target range for homocysteine is below 10 µmol/L in the serum.

Third Example: CRP Test

A measuring sequence of a CRP test (C-reactive protein, which is used mainly for differing between viral and bacterial inflammation) is illustrated as a third example.

A lysis reagent (1000 µl) is disposed as the first fluid in the mixing container 1. 5 µl of whole blood are sucked in with the capillary 22 of the dosing container 8. The dosing container 8 contains a latex reagent (250 µl). The lysis reagent is mixed with the whole blood sample first and a calibration value is measured. Thereafter the latex reagent is added in a dosed manner and the concentration value is determined photometrically after the chemical reaction. The test sequence occurs as in example 1.

The measuring range of the photometric measuring device is 0.2 mg/dl to 6 mg/dl for example.

Fourth Example: Variant of the INR/PT Test

In contrast to the first example, the first INR test reagent is present as a dry-chemical coating (e.g. recombinant thromboplastin), or as a gel, powder or tablet, in the mixing container 2, wherein the dosing container 8 contains the second INR reagent as a liquid reagent. A dosing container 8 according to FIG. 5 with a closure membrane 10 plus predetermined breaking point 20 and a funnel-shaped integrally formed part 25 (shown without the closing plunger 11 and the reagent 13) is used.

The sample—20 µl of capillary blood for example—is dosed in this case manually by means of the capillary to the mixing container 2, whereupon the dry-chemical coating can dissolve at least partly. The dosing container 8 with the liquid reagent (e.g. buffer solution) is inserted thereupon into the mixing container. The further test sequence occurs as shown in example 1.

The measuring range of the photometric measuring device is in this case INR 1-INR 6 for example.

The following advantages of the test set in accordance with the invention can be mentioned especially:

The user does not have to perform any separate pipetting steps.

High precision of the obtained sample volume.

Much time is saved in taking the sample.

Reduction in costs by avoidance of separate sample-taking devices.

The invention claimed is:

1. A test set for a photometric measuring device, comprising a mixing container which has a filling opening, and
   a cylindrical dosing container having a first end and a second end and which is insertable in a sealing manner into the filling opening of the mixing container, so that the second end thereof extends into the mixing container, said dosing container comprising:
   a cavity which extends to said second end,
   a closure membrane which closes said cavity at said second end,
   a closing plunger configured to be axially displaceable in the cavity from the first end of the dosing container toward the second end to generate a predeterminable filling pressure in a liquid reagent in the cavity, and
   wherein the dosing container comprises a base with an opening at said second end,
   the closure membrane includes a linearly extending material taper, configured to provide a predetermined breaking point, which breaks open when the filling pressure is exceeded in a defined manner, triggered by an axial movement of the closing plunger, and
   wherein the linearly extending material taper is arranged eccentrically in the region of the opening in the base of the cylindrical dosing container.

2. The test set according to claim 1, wherein the closure membrane is injected, onto the second end of the dosing container.

3. The test set according to claim 1, wherein the filling pressure in the cavity of the dosing container lies in a range of <2 bars and the burst pressure of the predetermined breaking point of the closure membrane lies in the range of >3 bars.

4. The test set according to claim 1, wherein the closure membrane comprises a tapering, funnel-shaped, integrally attached formed portion which carries away from the dosing container.

5. The test set according to claim 1, wherein the axially displaceable closing plunger is arranged entirely within the dosing container, wherein the cavity has a slightly smaller inside diameter in a region of the seal seat of the closing plunger than in a collar region situated outside of the seal seat.

6. The test set according to claim 1, wherein the dosing container comprises a sealing collar in a sealing region toward the filling opening of the mixing container.

7. The test set according to claim 6, wherein the closure membrane and the sealing collar are connected by a web extending along the dosing container.

8. The test set according to claim 1, wherein the dosing container comprises an integrated sample-taking device at the second end thereof, which sample-taking device is in contact with a liquid present in the mixing container after the insertion of the dosing container into the filling opening.

9. The test set according to claim 8, wherein the sample-taking device comprises a capillary which is open on both sides and whose volume lies between 5 µL and 50 µL.

10. The test set according to claim 1, wherein a handle element is integrally formed on the dosing container, which handle element delimits an annular space and can be sealed to the outside by an annular splash protection element.

11. The test set according to claim 10, wherein the annular splash protection element and the axially displaceable closing plunger can be produced as an integral injection-molded component, wherein thin, breakable or severable connecting webs are provided between the splash protection element and the closing plunger.

12. A photometric measuring method in which a sample liquid is mixed with a reagent present in a mixing container and with a liquid reagent, wherein the liquid reagent is present in a dosing container whose cavity is sealed at one end by an axially displaceable closing plunger and at the other end by a closure membrane covering an opening in a base of the cylindrical dosing container, including the following steps:
   a. opening of the mixing container;
   b. adding the sample liquid to the mixing container;
   c. inserting the dosing container containing the liquid reagent into a filling opening of the mixing container;
   d. mixing the sample liquid with the reagent to form a preliminary product;
   e. introducing a liquid reagent from the dosing container into the mixing container with pressure exerted on the reagent by the axially displaceable closing plunger until the closure membrane arranged on the dosing container breaks open at a predetermined breaking point and discharges a jet of the reagent exiting under pressure into the mixing container;

f. mixing the preliminary product and the liquid reagent to an end product;

g. photometrically measuring the chemical reaction in an analyzer, and h. calculating the concentration of at least one sample ingredient of the end product.

13. The measuring method according to claim 12, wherein a photometric calibration measurement is carried out after the mixing of the reagent with the sample liquid.

14. The measuring method according to claim 12, wherein the reagent is present in the mixing container in a liquid, gel-like, freeze-dried, powder or tablet form, or as a wall film.

\* \* \* \* \*